United States Patent [19]

Nelson

[11] Patent Number: 5,573,927
[45] Date of Patent: Nov. 12, 1996

[54] ANTIBIOTIC SUSCEPTIBILITY TEST

[76] Inventor: Wilfred H. Nelson, 166 Little Rest Rd., Kingston, R.I. 02881

[21] Appl. No.: 977,670

[22] Filed: Nov. 18, 1992

[51] Int. Cl.$^6$ .............................. C12Q 1/18; C12N 13/00; G01J 3/00

[52] U.S. Cl. .................. 435/32; 435/4; 435/29; 435/34; 435/173.1; 435/240.3; 435/808; 435/849; 436/63; 436/805; 356/300; 356/301; 356/342

[58] Field of Search .................... 435/32, 4, 29, 435/34, 173.1, 240.3, 808, 849; 436/63, 805; 356/300, 301, 342

[56] References Cited

U.S. PATENT DOCUMENTS 4,847,198  7/1989  Nelson et al. ..................... 435/34

OTHER PUBLICATIONS

Krüger et al, *Experientia*, vol. 45, No. 4, pp. 322–325, Apr. 15, 1989.
Dalterio et al, *Chemical Abstracts*, vol. 104, p. 353, Ref. #105425m, 1986 (Appl. Spectrosc., 1986, 40(2), 271–272).
Monoharon et al, *J. Microbiol. Methods*, vol. 11, No. 1 pp. 1–15, 1990.
Nelson, *Chemical Abstracts*, vol. 110, p. 427, Ref. #169613C, 1989.
Britton et al, *Chemical Abstracts*, vol. 109, p. 367, Ref. #145618m. 1988 (Appl. Spectrosc. 1988 42(5) 782–788).
King et al, *J. Infect. Dis*, vol. 147, No. 4, pp. 758–764, Apr. 1983.

*Primary Examiner*—Elizabeth C. Weimar
*Assistant Examiner*—Abdel A. Muhamed
*Attorney, Agent, or Firm*—Samuels, Gauthier, Stevens & Reppert

[57] ABSTRACT

This invention relates to a method for biodetection and identification of antibiotic susceptibility tested in bacteria by cerating spectrum against target cells and comparing them.

2 Claims, 4 Drawing Sheets

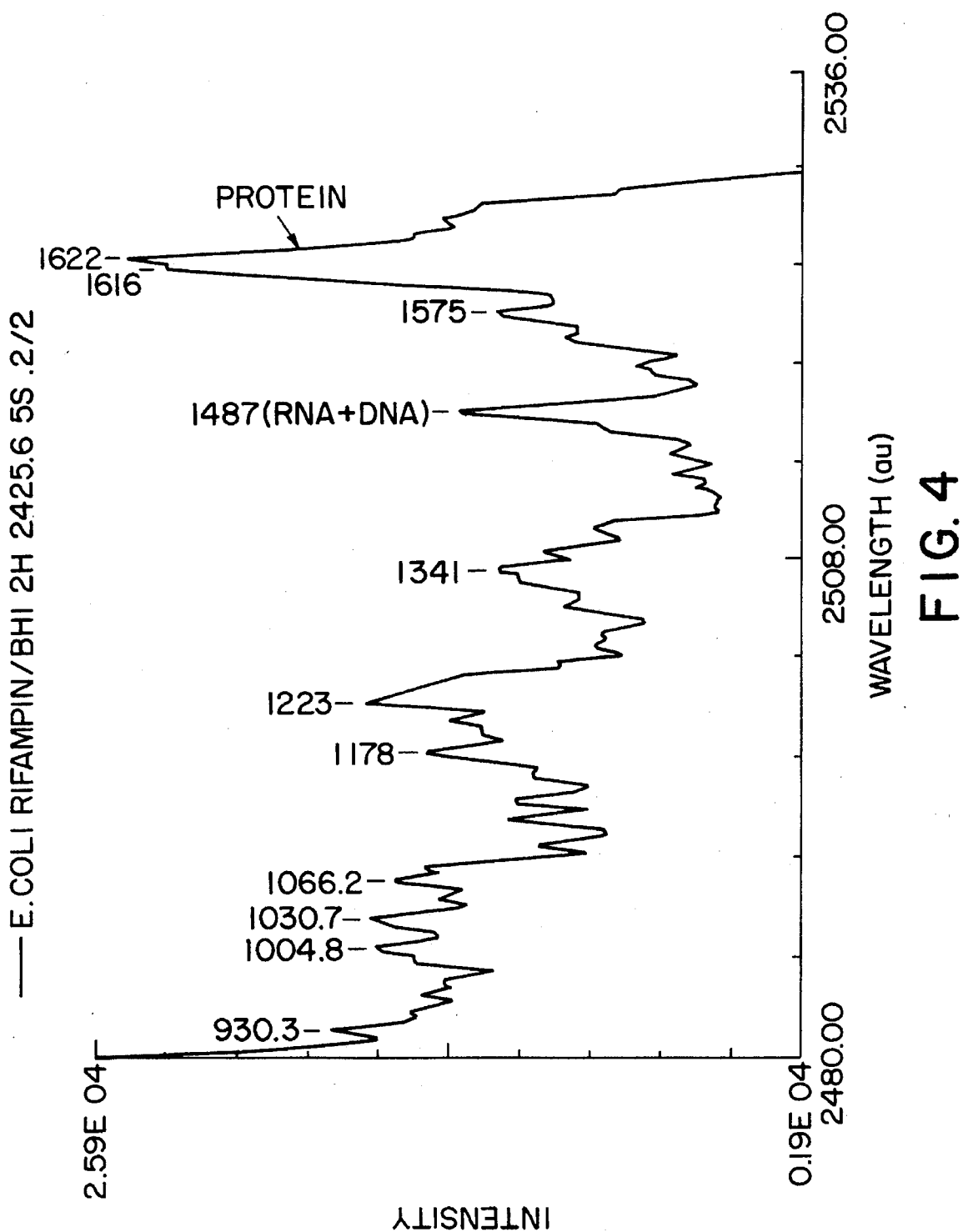

ANTIBIOTIC SUSCEPTIBILITY TEST

BACKGROUND AND BRIEF SUMMARY OF THE INVENTION

In selecting antibiotics for the treatment of bacterial infections, the selection process can vary from relatively straight forward to complex. For example, for streptococcus infections, the antibiotic of choice, penicillin, is well known in the field and can be prescribed with reasonably certainty that it will be effective. For a host of other infections, however, it is not so easily determined what the most efficacious antibiotic or combination of antibiotics will be. This is especially true with resistant strains of bacteria. Typically, the cells of the infecting organism are isolated, purified and then grown in culture in sufficient quantity such that they may be tested against various antibiotics. This is standard procedure. However, the isolation, purification and growth of the cells is normally a time consuming process, say ranging between 12 to 48 hours. In the case of slow growing mycobacteria, the process can be longer.

Common to antibiotic susceptibility tests has been the need to directly or indirectly measure the increase in the mass of a bacterial culture over time. This is accomplished in the presence and absence of antibiotics. Until recently, mass could only be determined conveniently by photometry. Today methods range from measurement of cellular ATP and the release of radioactive carbon dioxide from labelled substrate to release of fluorophores from fluorogenic substrates. Still, all these methods require the growth of the organism and generally need $10^5$–$10^7$ cells/inoculum. The use of large numbers of cells requires time consuming isolation and growth steps.

The last quarter century, and especially the last decade, has seen a revolution in the application of sensitive and rapid methods of chemical analysis. This has happened, to a large extent, due to advances in electronics, optics, and computer technology which have allowed the practical application of physical methods which previously had been understood in theory, but were too cumbersome to use. These methods have had a major impact on analytical laboratories by making previously difficult analyses affordable and routine by providing many opportunities for automation.

However, until relatively recently, there was little promise of applying these sophisticated new techniques to biodetection because of the lack of information regarding the molecular composition of microorganisms. Today, chemical information can be used effectively to establish relationships at all levels in the taxonomic hierarchy. Chemical properties, it appears, can and must be used in description of many genera and species.

The progress of biochemists and microbiologists in characterizing and identifying chemical markers has not gone unnoticed by chemical analysts. During the past several years, there has been marked progress in methods of chemical analysis and automation in biodetection and identification. Several potentially rapid new physical methods have been developed in the past several years which promise to achieve truly rapid analysis.

Among the most highly developed of the new rapid techniques is mass spectroscopy and its various combinations with gas chromatography (bacterial byproducts from cultures) and pyrolysis methods. Gas chromatography is highly effective in detecting characteristic bacterial metabolic products. Flow cytometry has provided means of the rapid detection, identification, and separation of cells. Total luminescence spectroscopy can detect organisms very rapidly. The various immunological methods also can be very specific and very rapid. All of these methods have their distinct advantages and disadvantages.

Mass spectroscopy may be unequalled in identification of pure cultures, and it is very rapid and sensitive. However, it is expensive to use, requires the destruction of samples, and is of questionable use in the analysis of complex mixtures. Flow cytometry is perhaps even more costly, requires extensive sample preparation, and in many aspects is limited in its scope of applicability. Luminescence techniques are of little use except in studies of pure cultures unless combined with immunological methods. Immunological methods are unequalled in specificity and speed, as well as sensitivity. Yet, they are often impractical to use unless very expensive and perishable materials are available in a state of constant readiness. Such methods are not practical for a wide range of organisms. Gas chromatography requires that cells be grown and, hence, this method is generally slow and of limited applicability.

In U.S. Pat. No. 4,847,198, a system for the rapid detection and identification of bacteria and other microorganisms is disclosed. A beam of visible or ultraviolet light energy contacts a microorganism under investigation. A portion of the light energy is absorbed by the microorganism and a portion of the light energy is 'emitted' from the sample at a lower energy level. The emitted light energy (resonance enhanced Raman scattering) may be measured at any angle but preferably is measured as back scattered energy. This energy is processed to produce spectra which are inherently characteristic of the microorganisms.

The light energy which contacts the microorganism can be at any wavelength so long as it corresponds to a molecular electronic transition which corresponds to strong absorption by the organism. Preferably, the energy is a single selected wavelength in the ultraviolet range since most electronic transitions of component molecules of microorganisms occur in that range.

In a preferred embodiment, the emitted energy measured is based upon ultraviolet resonance Raman spectroscopy. Bacteria under investigation are struck by an incident beam of light energy, typically a single wavelength in the ultraviolet range. The emitted energy is collected, collimated and focused onto the entrance slit of a monochromator. The beam strikes a grating or gratings and the wavelengths reflected by the grating or gratings are plotted versus intensity to obtain a spectrum.

The present invention is directed to a previously unrecognized use of the spectra generated according to the teachings of the '198 patent.

The inventive process enormously reduces or eliminates the purification and growth steps of the prior art and also eliminates the need for bacterial mass measurement in the final testing step. The invention utilizes the fact that in the life cycle of a cell exposed to enriched media, there is a phase prior to mitosis recoginized as the lag phase where the RNA accumulates significantly and rapidly. The effect of an antibiotic, rifampin, on this accumulation is used as a measure of its efficacy against the target cell.

The spectra of a first set of target cells as a control are plotted. Target cells then are placed into BHI or other enriched growth medium and divided into second and third sets. In the second set, the cells are cultured under optimal conditions. In the third set, the cells are cultured under the same optimal conditions as the second set but an antibiotic is added to the culture of the second set. Prior to mitosis the cells of the sets are analyzed and the spectra plotted and compared.

In the preferred embodiment of the invention, with E. coli the target cell, the affect on the ribosome peaks are compared to determine the efficacy of the antibiotic. This peak was selected because it reflects the rate of growth of ribosomes which increase in large amounts prior to rapid cell division. It has been found that other lesser peaks in the spectra can also be correlated to ribosomal growth rates and can be used to evaluate the efficacy of the desired antibiotic.

BRIEF DESCRIPTION OF THE DRAWINGS

FIG. 4 confirms that rifampin in MIC amounts inhibits the ribosomal development in *E. coli*.

DESCRIPTION OF THE PREFERRED EMBODIMENT(S)

Figure 1:
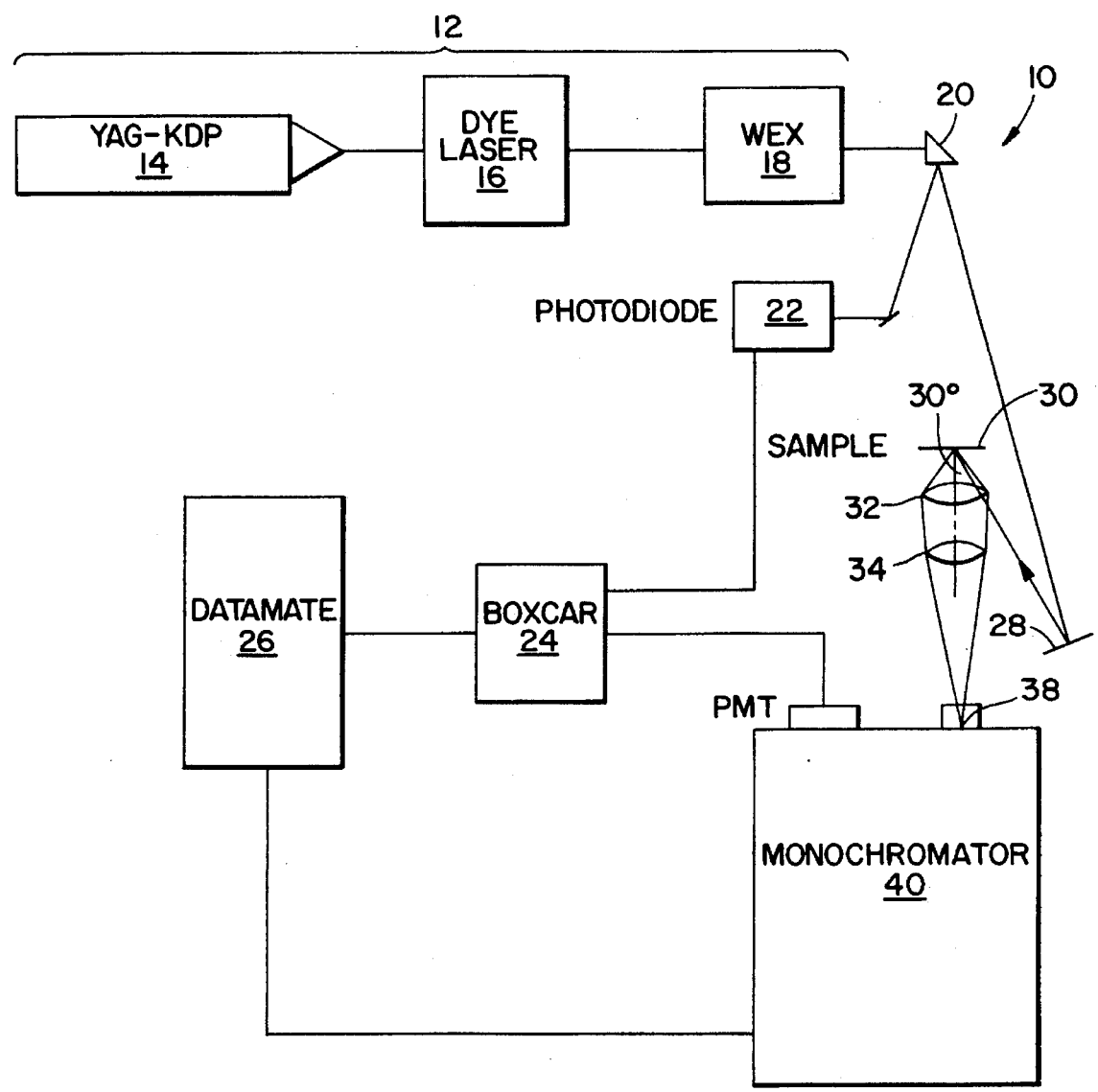
FIG. 1 is a schematic representation of a system embodying the invention.

A schematic representation of a system 10 used for the method of the invention is shown in FIG. 1. A light source 12 comprises three major components: a Nd-Yag (Quanta-Ray DCR-1A) laser 14 which produces high energy light pulses at 1064 nm, 532 nm, 355 nm, and 266 nm, a dye laser 16 (Quanta-Ray PDL-2) which shifts pulse energies from Yag frequencies to lower energies, and a wavelength extender 18 (WEX: Quanta Ray) which either doubles the dye laser output or mixes the dye-laser output or doubled dye laser output with an Nd-Yag fundamental to produce pulsed UV light at a wavelength between 350–216 nm. The output from the wavelength extender 18 strikes a split prism 20 which produces two beams. A first reference beam strikes a mirror and is reflected onto a photodiode 22. The output from the photodiode is transmitted to a Princeton Applied Research Model 162 Boxcar Averager 24. A Spex Datamate DM01 microcomputer 26 controls the stepping motor (not shown) of a monochromator 40, general data acquisition and disc storage of spectra.

The second beam from the prism 20 strikes a mirror 28 which directs the beam to a sample 30 under investigation. The energy back scattered from the sample is collimated by a lens 32, condensed by an optically aligned lens 34 and focused by the lens 34 on an entrance slit 38 of the monochromator 40.

The formation of a single wavelength in the ultraviolet range, the use of that wavelength to create spectral information about a specimen and the control and output of that information in various graphic or tabular forms is within the scope of those skilled in the art. Where the present invention primarily differs from prior art techniques is in the collection and use of back scattered energy, i.e. resonance enhanced Raman scattering from a microorganism. The invention will be described with particular reference to the following Example, which Example is illustrative of and not a limitation of the scope of the invention.

EXAMPLE

The laser 14 contained an angle tuned crystal harmonic generator which doubled a 1064 nm Yag output to 532 nm. This 532 nm output was used to pump the dye laser 16 which, in turn, emitted a beam at 627.8 nm. The extender 18 then frequency doubled the dye laser output and mixed it with the Yag 1064 nm fundamental to obtain the 2424.0 A output used. Alternatively, the output of an argon ion laser can be frequency doubled to produce output at 244 nm or 257 nm.

The monochromator 40 was a Spex Model 1702:0.75 meter single grating unit with wavelength drive. A 3600 line/mm grating was employed in the first order for maximum UV grating efficiency. Entrance and exit slits were set at 200 um for all spectra. The detector used was a Hamamatsu R 166UH high gain "solar blind" tube which is insensitive to wavelengths longer than 320 nm. Cathode voltage was 900 v. Use of the "solar blind" tube minimized stray light interference originating from fluorescing biological samples. The Spex Datamate microcomputer 26 controlled the stepping motor of the monochromator and general data acquisition.

The Boxcar Averager 24 was combined with two Model 166 Gated Integrators (not shown) and used for signal recovery. The photodiode 22 monitored the double dye laser output and was used to trigger the average as well as to provide a signal proportional to the laser power for use in signal rationing against the PMT signal channel to compensate for pulse-to-pulse laser intensity variations. A 15 ns aperture duration was used to capture the PMT signal and a 100 s time constant was used in each gated integrator. Scan speeds of 12s/0.2 A and 10s/0.1 A were used resulting in scan times of 53 and 88 minutes, respectively, for 900–1750 $cm^{-1}$ scans. The wavelength calibration was by means of standard mercury lines.

The sample cell 30 was a 2-inch length cell of 4 mm 0.3., 3 mm i.d. suprasil quartz tubing. The samples were continuously recirculated with a Masterflex tubing pump (Cole Parmer Instrument Co.). A flow rate of 15 ml/minute was used for sample volumes of 10 ml for chemicals and 4 ml for bacterial suspensions.

All test samples were composed of suspensions of bacterial cultures. Specifically, Escherichia coli ATCC 25922 was obtained from the American Type Culture Collection, Rockvile, M.d. Stock cultures were maintained at 4° C. following incubation at the proper growth temperatures for 24 hours. Experimental samples were obtained by inoculating a TSB broth with bacteria and incubating the culture for 24 hours. The bacteria were isolated by centrifugation and washed in sterile0.85% saline. The bacterial density after dilution was approximately $10^8$–$10^9$ organisms/ml to accomodate the bulk sample cell 30. A first set of cells was initially analyzed as described below and the spectra plotted, FIG. 2.

The remaining bacterial culture was divided into second and third sets. The second set cultured at optimal growth conditions and the third set cultured at optimal growth conditions together with the addition of an antibiotic, specifically rifampin, in an amount determined from the minimal inhibitory concentration, 10 mg/ml. The spectra of FIG. 3 and 4 were taken after approximately two hours. Prior to mitosis, the first and second sets, FIGS. 3 and 4 respectively, were analyzed as described below and spectra generated. The cell numbers were established by optical absorption. Because the optical absorption did not change over the life of the experiment, it could be assumed that the uninhibited culture remained in a lag phase of growth.

The excitation beam from the extender 18 was focused onto the sample cell 30 with a 10 cm focal length lens 28 placed 8.3 cm from the sample cell. To minimize the effect of sample optical density on the scattered light intensity, 300° back-scattering geometry was used. The scattered light was collected with a 2-inch diameter 6.5 cm focal length quartz lens 32 and focused onto the entrance slit 38 of the monochromator with a 35.0 cm focal length quartz lens 34. Because of the highly scattering nature of the bacterial samples, a filter was devised to exclude Rayleight scattering. For this purpose a 0.7 mM solution of quinoline in 1.0M HCl was placed in a 1 cm path length cuvette in front of the entrance slit. The quinoline efficiently absorbs 2424 A light while transmitting 40–50% of light in the range 247–260 nm (The Raman range). The average laser beam power at the sample was 2–3 mW. (A second monochromator or atomic line filter would serve to exclude Rayleight scattered light more efficiently).

Figure 2:
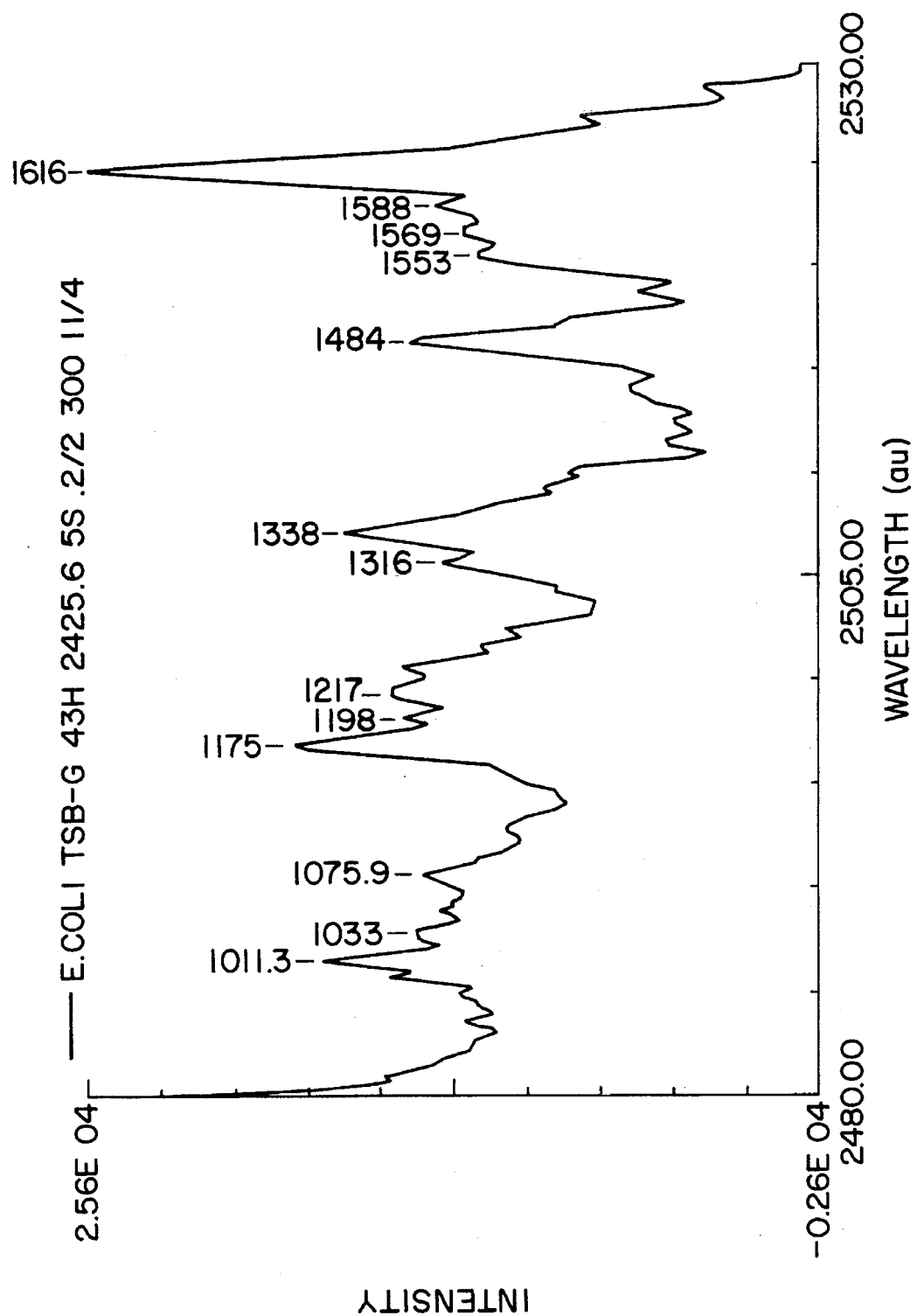
FIG. 2 shows the resonance Raman spectra of an original inoculum excited at 242 nm.
Figure 3:
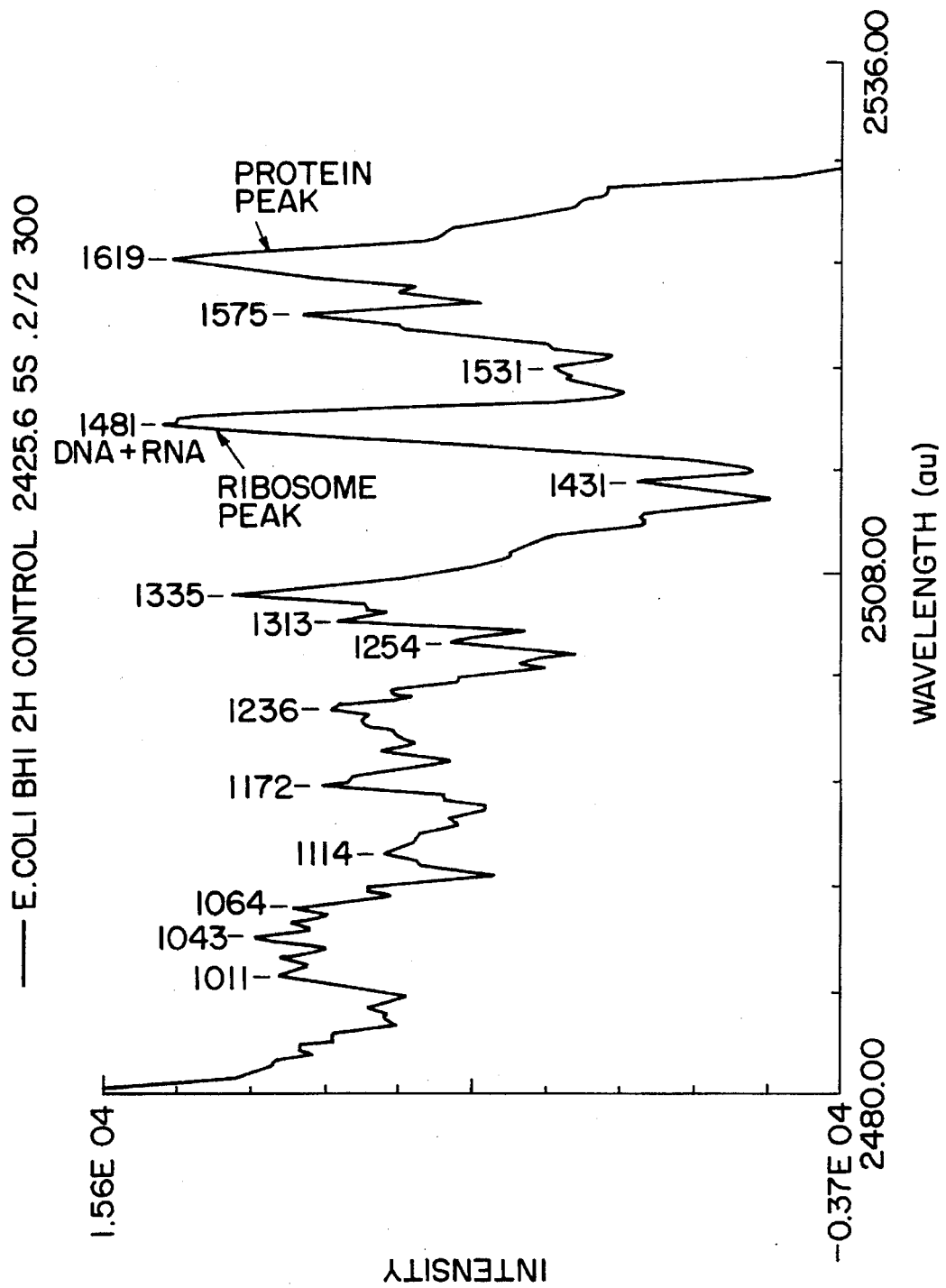
FIG. 3 shows the result of rapid ribosomal growth prior to cell division.

The spectra shown in FIGS. 2, 3 and 4 were taken using a single wavelength of 242 nm. FIG. 2 shows the spectra of the *E. coli* of the initial culture. FIG. 3 shows the spectra of the second set of *E. coli* in growth media which illustrates the rapid build-up of ribosomes in the lag phase. FIG. 4 is *E. coli* in growth media treated with the antibiotic showing basically no growth in the ribosome curve.

Comparisons for the ribosome peak at 1481 wavelength clearly illustrates that the ribosome necessary for growth of the cells is substantially inhibited. That is, the spectra allows one to recognize and predict that growth will not occur even before cell divisions normally occur.

Single cell detection is possible if a microscope-equipped system is used with a CW source which will not damage the samples. Truly rapid analysis should be possible if an optical multichannel analyzer is used for detection rather than the present scanning system. It is anticipated that a library of spectra will be obtained and placed in storage such as on disc which can be rapidly scanned by a computer allowing rapid identification on the basis of resonance Raman spectra.

Our invention has been described with reference to a specific geometric configuration for the collection of back scattered energy. It is within the scope of this invention that back scattered energy may be collected by any suitable technique within an angular range from 0° to 90° and preferably within a range of from 0° to 45° with the angular relationship being defined as the angle between the incident beam and the axis along which the back scattered energy is collected.

The generation of the characteristic spectra was described in reference to a mechanically driven eschelle grating. other techniques which would be suitable of purposes of the invention to ultimately display the unique spectra associated with the microorganism under examination include the combination of a spectrograph and a multichannel analyzer. It would be possible in principal to use photographic detection as well.

In the preferred embodiment, a specific bacterium was described. It is believed that any of the gram negative or gram positive bacteria can be so analyzed.

In the Example, the test samples were suspensions of bacterial cultures. the microorganisms may be embodied in any biologically acceptable carrier or medium wherein the sample microorganisms will emit energy which will produce spectra characteristic of the microorganism.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described our invention, what we now claim is:

1. A method for determining the effectiveness of an antibiotic against a bacteria which comprises:

displaying Raman spectra of a first set of target cells of an initially cultured bacteria *E. coli;* culturing said target cells of a second set in a growth medium free of antibiotic;

displaying the Raman spectra of the cells of the second set prior to mitosis;

culturing said target cells of a third set in a growth medium containing an antibiotic of interest;

displaying the Raman spectra of the target cells of the third set prior to mitosis; and displaying ribosome peaks and comparing the ribosome peaks of the spectra of the second and third sets.

2. The method of claim 1 wherein the antibiotic is rifampin.

\* \* \* \* \*

UNITED STATES PATENT AND TRADEMARK OFFICE
CERTIFICATE OF CORRECTION

PATENT NO. : 5,573,927
DATED : Nov. 12, 1996
INVENTOR(S) : Wilfred H. Nelson

It is certified that error appears in the above-indentified patent and that said Letters Patent is hereby corrected as shown below:

Column 1, after the title of the invention, insert --

The U.S. Government has a paid-up license in this invention and the right under limited circumstances to require the patent owner to license others on reasonable terms as provided for by the terms of Grant No. DAAD 0593W0855 awarded by the Department of the Army.

Signed and Sealed this

Twenty-fifth Day of March, 1997

*Attest:*

BRUCE LEHMAN

*Attesting Officer*  *Commissioner of Patents and Trademarks*